United States Patent [19]
de la Poterie

[11] Patent Number: 6,113,925
[45] Date of Patent: *Sep. 5, 2000

[54] METHOD OF FORMING A FILM USING A COMPOSITION CONTAINING A FLUOROALKYL COPOLYMER

[75] Inventor: Valérie de la Poterie, Le Châtelet En Brie, France

[73] Assignee: L'Oreal, France

[*] Notice: This patent issued on a continued prosecution application filed under 37 CFR 1.53(d), and is subject to the twenty year patent term provisions of 35 U.S.C. 154(a)(2).

[21] Appl. No.: 08/668,226

[22] Filed: Jun. 21, 1996

Related U.S. Application Data

[63] Continuation-in-part of application No. 08/651,533, May 22, 1996, Pat. No. 5,911,973, and a continuation of application No. 08/358,619, Dec. 14, 1994, abandoned.

[30] Foreign Application Priority Data

Dec. 15, 1993 [FR] France .................. 93 15069

[51] Int. Cl.$^7$ .............. A61K 6/00; A61K 7/00; A61K 7/04; A61K 31/74
[52] U.S. Cl. .............. 424/401; 424/61; 424/70.1; 424/78.03
[58] Field of Search .............. 424/78.03, 401, 424/70.7, 62, 70.11

[56] References Cited

U.S. PATENT DOCUMENTS

| | | |
|---|---|---|
| 3,822,228 | 7/1974 | Petrella et al. . |
| 3,959,462 | 5/1976 | Parks et al. . |
| 4,135,524 | 1/1979 | Rosenberg et al. . |
| 5,136,000 | 8/1992 | Luttenberger et al. . |

FOREIGN PATENT DOCUMENTS

| | | |
|---|---|---|
| A 0195714 | 9/1986 | European Pat. Off. . |
| A 0206671 | 12/1986 | European Pat. Off. . |
| A 0473148 | 3/1992 | European Pat. Off. . |
| A 0554667 | 8/1993 | European Pat. Off. . |
| A 0558423 | 9/1993 | European Pat. Off. . |
| 2 069 289 | 9/1971 | France . |
| 2 175 332 | 10/1973 | France . |
| 2 282 857 | 3/1976 | France . |
| 2 385 391 | 10/1978 | France . |
| 2 540 131 | 8/1984 | France . |
| 4-210613 | 12/1990 | Japan . |
| 4-210 613 | 7/1992 | Japan . |
| WO 92/16103 | 10/1992 | WIPO . |

OTHER PUBLICATIONS

Derwent Abstract No. 000979474 of French Pat. Appln. 2,175,332, Oct. 19, 1973.
Derwent Abstract No. 004049707 of French Pat. Appln. 2,540,131, Aug. 3, 1984.
Derwent Abstract No. 004750319 of European Pat. Appln. 0195714, Sep. 24, 1986.
Derwent Abstract No. 009550481 of European Pat. Appln. 0554667, Aug. 11, 1993.
Derwent Abstract No. 009581282 of European Pat. Appln. 0558423, Sep. 1, 1993.
Derwent Abstract No. 920304635 of Japanese Pat. Appln. 4210613, Jul. 31, 1992.

*Primary Examiner*—Thurman K. Page
*Assistant Examiner*—S. Howard
*Attorney, Agent, or Firm*—Finnegan, Henderson, Farabow, Garrett & Dunner, LLP

[57] ABSTRACT

The invention relates to a method for forming a film which may be used as a mascara, an eye-liner, a nail varnish or a lacquer, by applying to eyelashes, hair, nails, or skin a film-forming composition in an aqueous medium, containing, in dispersed form, at least one film-forming material and a fluoro copolymer resulting from the copolymerization of at least a first fluorovinyl monomer and at least a second monomer of formula (A):

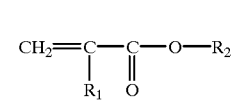

(A)

where $R_1$ represents a hydrogen atom or a $C_1$ to $C_4$ alkyl radical and $R_2$ represents a $C_1$ to $C_6$ alkyl radical, a $C_2$ to $C_4$ hydroxycarbon radical or a radical —$(CH_2)_p$—NH—$R_3$, where $R_3$ represents a $C_1$ to $C_6$ alkyl or a cycloalkyl and p is an integer ranging from 1 to 4, for a time sufficient to form the film.

7 Claims, No Drawings

METHOD OF FORMING A FILM USING A COMPOSITION CONTAINING A FLUOROALKYL COPOLYMER

This application is a continuation-in-part of co-pending U.S. application Ser. No. 08/651,533, filed May 22, 1996 now U.S. Pat. No. 5,911,973 as a continuation of Ser. No. 08/358,619, filed Dec. 14, 1994, now abandoned, which is hereby incorporated by reference in its entirety.

The subject of the invention is a film-forming composition containing a fluoroalkyl copolymer, which may in particular be used in the cosmetics field for making up and/or caring for the face and/or the hair. The composition of the invention may be used as an eye-liner, a mascara or a lacquer, and especially as a nail varnish, which may be coloured or colourless.

More precisely, the invention relates to a composition which has an aqueous medium containing film-forming polymers, which composition is capable of forming a homogeneous and continuous film on a support (eyelash, hair or nail).

Water-based nail varnishes are make-up products that are currently in full development for the purpose of replacing solvent-based varnishes, not only for reasons of consumer safety, but also for environmental reasons, i.e., because of the absence of volatile compounds in such formulations. The new make-up products should, nevertheless, possess equivalent cosmetic characteristics of quality to those of solvent-based nail varnishes. These qualities are recognized by a person skilled in the art as including easy application, rapid drying of the film, production of a shiny film that adheres to the surface of the nail, good staying power over time and, more particularly, good water-resistance. In addition, these products should be non-irritating towards the skin and the nails.

Water-based nail varnishes, however, often have the drawback of poor staying power over time due primarily to poor water-resistance. For example, the film in such varnishes may redissolve in water, may tarnish in the presence of water, may turn white under the action of water, or may become detached in water.

In order to avoid the problems of water-resistance, it may be envisioned either to use polymers that are not capable of dissolving in water, although this is sometimes not sufficient to avoid some of the other drawbacks mentioned above, or to use additives that will prevent water from penetrating and from detaching the film by repelling it or by making it slide over the film. Essentially, these additives would protect the nail varnish film from water.

In the hair field, aqueous washing compositions containing fluoroalkyl copolymers derived from a copolymerization of a fluoroacrylic monomer and an aminoacrylic monomer are known from French Patent Application FR-A-2,385,391 and U.S. Pat. No. 4,135,524, the disclosures of which are hereby incorporated by reference. These water-insoluble copolymers are suspended in water using surfactants. Their aim is to improve the time taken to dry treated hair. However, the formation of a homogeneous and continuous film is absolutely impossible with these compositions.

Fluoroalkyl copolymers derived from a copolymerization of a fluoroacrylic monomer and an acrylic monomers containing an alkyl, hydroxyalkylene or alkylamino radical are described in document WO-A-92/16103, the disclosure of which is hereby incorporated by reference. These copolymers are disclosed as protecting active substances present in herbicides, insecticides or pesticides from water or from oil, for the purpose of enhancing their effectiveness. WO-A-92/16103 teaches dispersing them in water using surfactants. As above, the formation of homogeneous and continuous films, intended particularly for the cosmetics field, is not possible with these compositions.

European Application EP-A-0,206,671, the disclosure of which is hereby incorporated by reference, also discloses the use of fluoroalkyl copolymers. These copolymers are dissolved in a volatile oil or an organic solvent, typically in lipsticks, mascaras, eye-liners and nail varnishes. Such cosmetic products have the drawback of containing a high proportion of oil and/or of organic solvent for dissolving these polymers, and these oils and solvents may, under certain circumstances, be harmful to the environment.

The present invention is drawn to a new film-forming composition in an aqueous medium, which may be used in cosmetics, that aims to eliminate the drawbacks and disadvantages described above. The composition of the invention possesses particularly good water-resistance and good staying power over time, while also retaining good cosmetic properties and a pronounced ability to form homogeneous and continuous films.

The inventors have found, surprisingly, that the incorporation of a fluoroalkyl copolymer in emulsion, in an aqueous cosmetic composition, imparts good water-resistance thereto. More precisely, the present invention is directed to a film-forming composition in an aqueous medium, comprising, dispersed in the aqueous medium, at least one film-forming material and a fluoro copolymer resulting from the copolymerization of at least a first fluorovinyl monomer and at least a second monomer of formula (A):

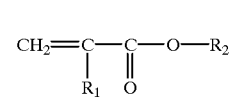

(A)

where $R_1$ represents a hydrogen atom or a $C_1$ to $C_4$ alkyl radical and $R_2$ represents a $C_1$ to $C_6$ alkyl radical, a $C_2$ to $C_4$ hydroxycarbon radical or a radical —$(CH_2)_p$—NH—$R_3$, where $R_3$ represents a $C_1$ to $C_6$ alkyl or a cycloalkyl and p is an integer ranging from 1 to 4.

In another embodiment, the present invention also relates to a film formed from a film-forming composition in an aqueous medium, the composition comprising, dispersed in said aqueous medium, at least one film-forming material and a fluoro copolymer resulting from the copolymerization of at least a first fluorovinyl monomer and at least a second monomer of formula (A) as described above, wherein the film formed has a resistance in water of $\geq 3$ hours.

In a further embodiment, the present invention relates to a method of forming a film on an eyelash, hair, nail or on skin. The inventive method comprises applying to a keratinous fiber, such as an eyelash, hair, or nail, or to skin a film-forming composition in an aqueous medium comprising, dispersed in said aqueous medium, at least one film-former and a fluoro copolymer resulting from the copolymerization of at least a first fluorovinyl monomer and at least a second monomer of formula (A) for a time sufficient to form the film. Preferably, the film formed is homogeneous and continuous.

"Fluoro" should be understood to mean a total or partial substitution of the hydrogen atoms of the alkyl chain by fluorine atoms. The substitution is preferably total.

"Hydroxycarbon radical" should be understood to mean a hydroxyalkyl or hydroxyalkenylene (i.e., an unsaturated alkyl substituted by a hydroxy group) radical.

In effect, the processes of film formation in an aqueous medium and in an organic solvent medium (for example, in the case of nail varnishes) are totally different. In an aqueous medium, the polymer particles are initially separate, and then bind together and interdiffuse progressively as the water evaporates from the support. In contrast, in an organic solvent medium, the polymer chains are bound together and interlinked at the start, even before applying the composition (varnish) to the support.

Thus, the fluoro copolymer of the present invention could have destroyed the film-forming ability of the composition, leading in particular to embrittlement and poor cohesion of the film, rendering it unusable. Against all expectations, and despite the nondissolution of these copolymers in water, however, the copolymers of the invention surprisingly impart good film-forming ability to the composition. In addition, the films obtained using these copolymers exhibit enhanced water-resistance relative to those resulting from the film-forming compositions of the prior art, which do not contain fluoro copolymers.

The composition of the invention may contain a water-miscible organic solvent in an amount of preferably less than 30% by weight and more preferably from 0% to 15% by weight. This low, or even zero, solvent content renders the composition less harmful, especially when used in a cosmetic, to the support on which it is placed.

Suitable solvents for use in the present invention include $C_1$ to $C_6$ alcohols (ethanol and isopropanol), ketones (acetone and methyl ethyl ketone), acetates such as butyl acetate and ethyl acetate, and saturated $C_5$ to $C_{12}$ hydrocarbons such as hexane or octane.

The first fluoro monomer is advantageously a monomer of the acrylic type which has the following formula (B):

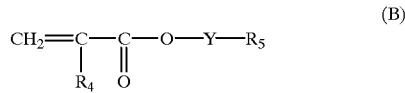

(B)

where $R_4$ represents a hydrogen atom or a $C_1$ to $C_4$ alkyl radical, Y represents a $C_1$ to $C_6$ alkylene radical (no unsaturation) and $R_5$ represents a $C_1$ to $C_{20}$ alkyl radical in which some or all of the hydrogen atoms are replaced by fluorine atoms.

According to the invention, the alkyl radicals, which may or may not contain fluorine, and the alkylenated radicals (alkylene and alkenylene) may be linear or branched.

For example, the first fluoro monomer may have the formula:

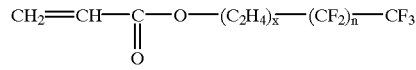

where n ranges from 4 to 16 and x is 1 or 2. In this formula, formula (B), $R_4$ is H; Y is —$C_2H_4$— or —$C_4H_8$— and $R_5$ is —$(CF_2)_n$—$CF_3$. Preferably, n is 5, 7, 9 or 11.

The first fluoro monomer may also have the formula:

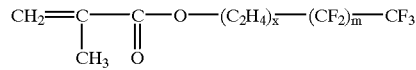

where m ranges from 4 to 16 and x is 1 or 2. According to the substituents in formula (B), $R_4$ is $CH_3$; Y is —$C_2H_4$— or $C_4H_8$— and $R_5$ is —$(CF_2)_m$—$CF_3$. Preferably, m is 5, 7, 9 or 11.

As the first fluoro monomer of the invention, there may also be mentioned the compounds of the type:

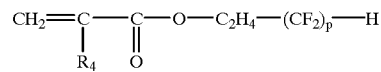

where $R_4$ is H or —$CH_3$ and p ranges from 6 to 16 and, preferably is 6 or 8.

Preferably, the second monomer is such that $R_1$ represents hydrogen or a $C_1$ to $C_4$ alkyl radical and, for example, a methyl, ethyl, n-butyl or isopropyl radical. In addition, the ratio by weight of the first fluoro monomer relative to the second non-fluoro monomer may range from 10/90 to 90/10 and, preferably, from 12/88 to 50/50.

The fluoro copolymers of the invention may be manufactured as described in documents FR-A-2,175,332, FR-A-2,540,131 and EP-A-206,671, the disclosures of which are hereby incorporated by reference. These copolymers include, for example, those sold by ATOCHEM under the brand name FORAPERLE® 344. FORAPERLE® 145, 333, 390 and 350, which are fluoroamine monomers, may also be used. These fluoro polymers are provided in the form of a dispersion in water, optionally containing a low amount of an alcohol and/or a ketone. This dispersion may be diluted in any proportion in water.

The copolymers according to the invention may be introduced into any aqueous composition based on aqueous dispersions of film-forming materials. The film-forming materials are preferably film-forming polymers, which include polyurethane dispersions, acrylic, vinylic or styrene-acrylic polymer dispersions or any other aqueous dispersion of polymers or copolymers which are compatible with the fluoro copolymers according to the invention in an aqueous medium. Preferred film-forming materials which may be used in the invention are, for example, film-forming polymers sold in the form of a dispersion in an aqueous solution by the company SANNCOR, such as SANCURE® 878, which is a polyurethane-polyether dispersed in water. These film-forming materials may be used in an amount preferably ranging from 2% to 60%, and more preferably from 4% to 30%, by weight of active material relative to the total weight of the composition.

The fluoro copolymers of the invention may be used as additives. They represent preferably from 0.005% to 10% by weight of active material relative to the total weight of the composition, and more preferably from 0.5% to 5%. These proportions are entirely suitable for the production of a water-based nail varnish.

The compositions of the present invention are preferably used in water-based nail varnishes. In addition to nail varnishes, the composition of the present invention may be used in mascaras, eye-liners or water-based lacquers.

Generally, any film-forming cosmetic composition which needs to be water-resistant can contain the composition of the present invention.

The composition of the invention makes it possible to obtain a dry extract, i.e., the percentage of the weight of the solid matter in the composition relative to the total weight of the composition, which may range from 20% to 60% and preferably from 25% to 45%.

Moreover, the composition of the invention may be colourless or coloured. In the latter case, at least one pigment of organic or inorganic nature, or an organic dye, is used. Among the organic pigments which may be used in the invention, there may be mentioned D&C Red No. 5, No. 6, No. 7, No. 10, No. 11, No. 12, No. 13 and No. 34, lacquers D&C Yellow No. 5 and D&C Red No. 2, and guanine. Suitable inorganic pigments that may be used include titanium dioxide, brown iron oxide, black iron oxide, red iron oxides, and bismuth oxychloride. These dyestuffs, when present, are generally used in an amount ranging from 0.01% to 25%, and preferably from 0.5% to 20%, by weight relative to the total weight of the composition.

The composition of the invention may additionally contain adjuvants in an amount, when present, preferably ranging from 0.01% to 10% by weight relative to the total weight of the composition, and more preferably less than 5%. The precise amount of additive depends on the adjuvant used, and may readily be determined by a person skilled in the art. Suitable adjuvants include those conventionally used in the cosmetics field, such as UV screening agents, preserving agents, wetting agents, dispersing agents or antifoam agents, waxes, drying or spreading accelerators, or alternatively compounds which enhance the shine or the hardness of the film obtained.

The compositions according to the invention may additionally contain at least one thickening agent in a proportion, when present, preferably ranging from 0.01% to 5%, and more preferably from 0.1% to 1%, by weight relative to the total weight of the composition. Among the thickening agents which are suitable for the formulation of these aqueous film forming compositions, there may be mentioned cellulose and derivatives thereof such as carboxymethylcellulose and hydroxyethylcellulose, silicates, clays such as laponite, synthetic polymers such as acrylic polymers or the associative polymers of polyurethane or hydroxyethylcellulose type which are modified by a hydrophobic chain, and natural gums such as carrageenan gum or xanthan gum. The preferred thickenings are hydroxyethylcellulose, laponite, and associative polyurethanes.

Moreover, the composition of the invention may contain a surface-active agent to emulsify the copolymers in water and thus to promote their dispersion. The surface-active agent which may be used in the invention in particular has an HLB (lipophilic/hydrophilic balance) value which is preferably $\geq 10$. It may be any commercially available, cosmetically acceptable hydrophilic agent. Preferred is a polyethoxylated nonionic compound of HLB=14, which is optionally associated with a quaternary ammonium containing a fatty chain. In general, from 0% to 10% by weight of surface-active agent is used relative to the total weight of the composition, and preferably from 3% to 5%.

The invention will be demonstrated by the following examples. The examples illustrate the characteristics and advantages of the present invention, but do not limit the present invention.

Since the invention is particularly suited for use as a nail varnish, Examples 1 to 6 which follow will deal with varnishes. Clearly, as indicated above, other cosmetic applications may be envisaged. Examples 7 and 8 illustrate two other types of cosmetic applications.

The compositions below were obtained with stirring, by dispersing the fluoro copolymers (FORAPERLE®) in water, optionally containing a preserving agent and a water-miscible solvent (an alcohol), and by adding to the dispersion the film-forming materials, the optional thickening agents, the waxes and then the pigments.

In the examples, the proportions are given in percent by weight.

EXAMPLE 1

Nail Varnish Composition (Control)

| | |
|---|---|
| Sancure ® 878 (37.5%)* | 75.0 |
| DC Red 30 | 0.5 |
| TiO$_2$ | 0.5 |
| Associative polyurethane thickening agent (SER AD Fx 1100 from the company SERVO) | 0.3 |
| Preserving agent | 0.04 |
| Water | qs 100 |

(*)The figures in brackets indicate the proportion of active material.

This varnish is easily applied to nails and it has a short drying time. The film obtained after drying is continuous, shiny and homogeneous.

EXAMPLE 2

Nail Varnish Composition

| | |
|---|---|
| Sancure ® 878 (39%)* | 70.00 |
| SER AD Fx 1100 | 0.3 |
| DC Red 30 | 0.5 |
| Preserving agent | 0.02 |
| Foraperle ® 145 (25%)* | 4.00 |
| Water | qs 100 |

The nail varnish of Example 2 has the same properties as those of the nail varnish of Example 1. The addition of FORAPERLE® thus conserves the cosmetic properties of the varnish. In addition, an enhancement in the water-resistance of the varnish is observed.

EXAMPLE 3

Nail Varnish Composition

| | |
|---|---|
| Sancure ® 878 (39%)* | 72.00 |
| SER AD Fx 1100 | 0.08 |
| DC Red 30 | 0.5 |
| Preserving agent | 0.02 |
| Foraperle ® 333 (28%)* | 3.6 |
| Isopropanol | 13.8 |
| Water | qs 100 |

The nail varnish of Example 3 has equivalent properties to those of the nail varnish of Example 2. The presence of a small amount of alcohol enhances its removal.

EXAMPLE 4

Nail Varnish Composition

| | |
|---|---|
| Sancure ® 878 (37.2%)* | 72.6 |
| Foraperle ® 145 (25%)* | 22.4 |
| SER AD FX 1100 | 0.08 |
| Pigments DC Red 30 | 0.5 |
| Preserving agents | 0.02 |
| Water | qs 100 |

The nail varnish of Example 4 has equivalent properties to those of the nail varnishes of Examples 2 and 3.

EXAMPLE 5

Influence of the Proportion of Fluoro Polymer in the Composition

Table I below gives the properties of the films obtained using the compositions of Examples 2, 4 and the following comparative example:

Comparitive Example

| | |
|---|---|
| Sancure ® 878 (37.2%)* | / |
| Foraperle ® 145 (25%)* | 80.0 |
| SER AD FX 1100 | 0.25 |
| Pigments DC Red 30 | 1.0 |
| Preserving agents | 0.05 |
| Water | qs 100 |

TABLE I

| Example | 2 | 4 | Comparative Example |
|---|---|---|---|
| Dry Extract (%) | 28.5 | 33 | 22 |
| Final % Foraperle ® | 1 | 5.6 | 20 |
| Brilliance of the film | 81.5 | 52.4 | 68.1 |
| Water-resistance | >3 H 30 | >4 H | <2 H 45 |

The brilliance corresponds to the coefficient of luminous reflectance of the film. The determination of the water-resistance will be explained hereinbelow.

From Table I, it is observed that in the compositions of the invention, FORAPERLE® does indeed enhance the water-resistance at the 1% or 5% concentration, but substantially reduces the brilliance of the film at the 5% concentration, which is undesirable. In order to be cosmetically satisfactory, a film should have a brilliance $\geq 75$.

When FORAPERLE® is used alone (comparative example), the brilliance of the film obtained is not good (rather dull film); its water-resistance is average and its covering power is nonexistent (at least 3 coats are necessary).

Thus, FORAPERLE® may indeed be used as an additive, in combination with another aqueous film-forming dispersion, preferably at a percentage of <5%.

EXAMPLE 6

Water-Resistance of the Varnish

Comparative tests relating to water-based nail varnish bases, in accordance with the invention and with the prior art, are given below.

The water-resistance of the films obtained may be controlled in two different ways:

either by observing the behaviour of each film obtained on keratin, stirred in hot water (45° C.) and surfactant;

or by depositing a drop of water on each film obtained and by measuring the angle which this drop forms with the film of the varnish. The higher the angle, the more the water is repelled by the surface on which it is deposited.

These two tests were performed on water-based nail varnishes based on a polyurethane dispersion (SANCURE® 878) containing a fluoro copolymer, in accordance with the invention, and not containing any fluoro copolymer, in accordance with the prior art.

Test of Resistance of the Film in Water

The varnish is applied to a sample of keratin which is left to dry at constant humidity and temperature for 1 hour. The keratin sample is then stirred in hot water (45° C.) in the presence of detergent (1% TEEPOL®). The behaviour of the film is then observed: whitening, decoloration, solubilization, detachment as a function of time.

The results are given in Table II below:

TABLE II

| Trial Composition | Result Obtained |
|---|---|
| without fluoro copolymer: Example 1 | detachment of the film before 8 min |
| with 1% A.M. *Foraperle ® 145: Example 2 | slight whitening, no detachment after 3 hours |
| with 1% A.M. *Foraperle ® 333: Example 3 | no whitening, no detachment after 3 hours |

(*) A.M. = Active material

It is indeed observed, from Table II, that the trial compositions with the copolymers according to the invention are more water-resistant than the trial composition without copolymer.

Water Drop Test

The angle formed by a drop of water with the surface of the film of varnish obtained is measured for each trial composition tested.

The results are given in Table III below. It is observed, from Table III, that the angles obtained with the trial compositions according to the invention are larger than those of the trial composition without copolymer. This shows that the films obtained according to the invention repel water more than the trial composition without copolymer.

TABLE III

| Trial Composition | Angle with water, in degrees |
|---|---|
| without copolymer: Example 1 | 69.3 |
| with 1% A.M. * Foraperle ® 145: Example 2 | 73.0 |
| with 1% A.M. *Foraperle ® 333: Example 3 | 79.5 |

EXAMPLE 7

"Mascara" Composition

| | |
|---|---|
| Beeswax | 10.0 |
| Carnauba wax | 2.0 |
| Paraffin | 7.0 |
| Triethanolamine stearate | 10.0 |
| Black iron oxide | 3.0 |
| Ultramarine blue | 1.5 |
| Gum arabic | 2.0 |
| Hydroxyethylcellulose | 1.0 |
| Panthenol | 1.0 |
| Preserving agents | 0.3 |
| Aqueous film-forming dispersion (34%)* (SANCURE ® 2060) | 15.0 |
| Foraperle ® 145 (25%)* | 4.0 |
| Water | qs 100 |

When applied to the eyelashes, the mascara has good water-resistance.

EXAMPLE 8

"Eye-liner" Composition

| | |
|---|---|
| Polyvinyl alcohol | 2.0 |
| Propylene glycol | 5.0 |
| Hydroxyethylcellulose | 0.1 |
| Laponite | 0.2 |

| | |
|---|---|
| Sodium lauryl sulphate | 0.1 |
| Black iron oxide | 15.0 |
| Aqueous film-forming dispersion (34%)* (SANCURE ® 2060) | 14.7 |
| Foraperle ® 145 (25%)* | 4.0 |
| Water | qs 100 |

When applied, the eye-liner has good water-resistance.

What is claimed is:

1. A method of forming a film on an eyelash, hair, nail or on skin, comprising the step of
applying to said eyelash, hair, nail, or skin a film-forming composition in an aqueous medium comprising, dispersed in said aqueous medium, a mixture of:
an aqueous dispersion of at least one film-former, wherein said film former is a polyurethane, and
an aqueous dispersion of a fluoro copolymer resulting from the copolymerization of at least a first fluorovinyl monomer and at least a second monomer of formula (A):

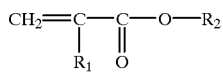
(A)

where $R_1$ represents a hydrogen atom or a $C_1$ to $C_4$ alkyl radical and $R_2$ represents a $C_1$ to $C_6$ alkyl radical, a $C_2$ to $C_4$ hydroxycarbon radical or a radical $—(CH_2)_p—NH—R_3$, where $R_3$ represents a $C_1$ to $C_6$ alkyl or a cycloalkyl and p is an integer ranging from 1 to 4, for a time sufficient to form said film.

2. A method according to claim 1, wherein said film formed is homogeneous and continuous.

3. A method of forming a film on a keratinous fiber or skin, comprising the step of applying to said keratinous fiber or skin a film-forming composition in an aqueous medium comprising, dispersed in said aqueous medium, a mixture of:
an aqueous dispersion of at least one film-former, wherein said film former is a polyurethane, and
an aqueous dispersion of a fluoro copolymer resulting from the copolymerization of at least a first fluorovinyl monomer and at least a second monomer of formula (A):

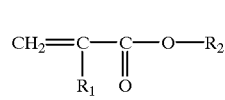
(A)

where $R_1$ represents a hydrogen atom or a $C_1$ to $C_4$ alkyl radical and $R_2$ represents a $C_1$ to $C_6$ alkyl radical, a $C_2$ to $C_4$ hydroxycarbon radical or a radical $—(CH_2)_p—NH—R_3$, where $R_3$ represents a $C_1$ to $C_6$ alkyl or a cycloalkyl and p is an integer ranging from 1 to 4, for a time sufficient to form said film.

4. A method according to claim 3, wherein said film formed is homogeneous and continuous.

5. A method according to claim 1, wherein said at least one film-forming polymer is a polyurethane-polyether or a polyurethane-polyester.

6. A method according to claim 3, wherein said at least one film-forming polymer is a polyurethane-polyether or a polyurethane-polyester.

7. A method of forming a film on a nail, comprising the step of
applying to said nail a film-forming composition in an aqueous medium comprising, dispersed in said aqueous medium, a mixture of:
an aqueous dispersion of at least one film-former, and
an aqueous dispersion of a fluoro copolymer resulting from the copolymerization of at least a first fluorovinyl monomer and at least a second monomer of formula (A):

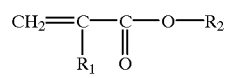
(A)

where $R_1$ represents a hydrogen atom or a $C_1$ to $C_4$ alkyl radical and $R_2$ represents a $C_1$ to $C_6$ alkyl radical, a $C_2$ to $C_4$ hydroxycarbon radical or a radical $—(CH_2)_p—NH—R_3$, where $R_3$ represents a $C_1$ to $C_6$ alkyl or a cycloalkyl and p is an integer ranging from 1 to 4, for a time sufficient to form said film.

* * * * *